June 8, 1943. H. W. DONAHEY Plant Pat. 588
PEACH TREE
Filed Aug. 20, 1940
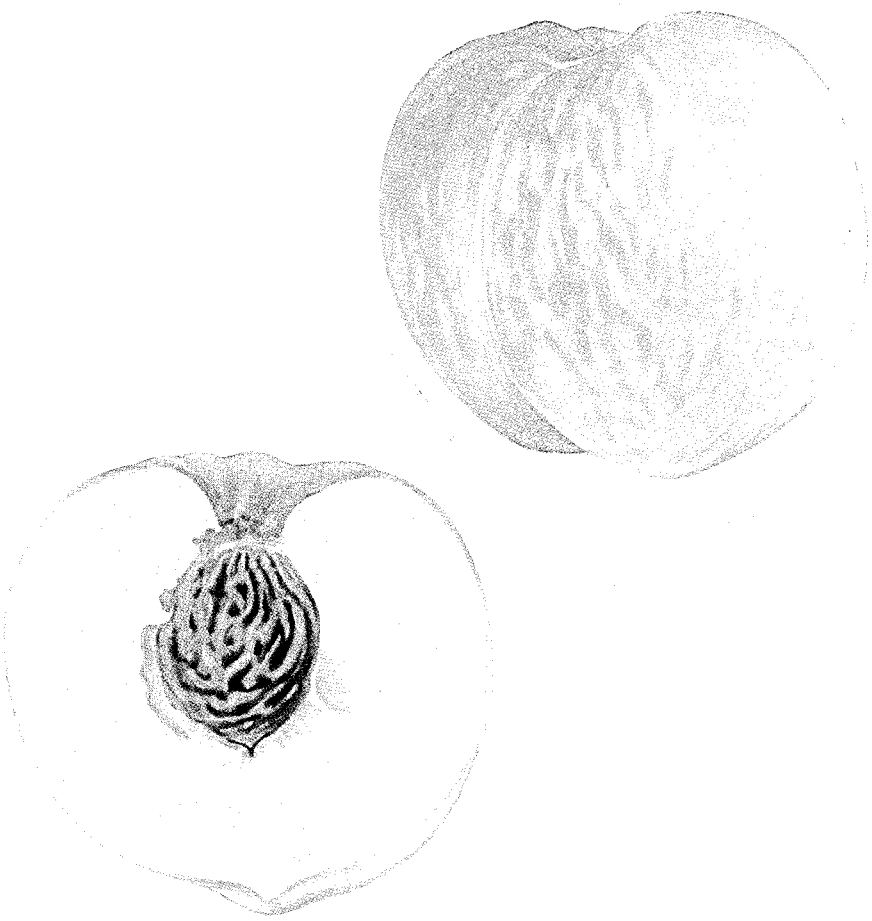
INVENTOR
Herbert W. Donahey
By Orville M. Kile
PLANT PATENT AGENT Patented June 8, 1943

Plant Pat. 588

UNITED STATES PATENT OFFICE

588

PEACH TREE

Herbert W. Donahey, Yakima, Wash., assignor to Columbia & Okanogan Nursery Company, Wenatchee, Wash.

Application August 20, 1940, Serial No. 353,436

1 Claim. (Cl. 47—62)

My present discovery relates to a new and improved variety of peach tree of the general J. H. Hale type but with some very important differences.

This new variety was discovered by me as a chance seedling of unknown parentage, growing in my garden where seeds had been discarded at canning time. As soon as the tree bore its first fruit, I recognized that this fruit was of extraordinary quality. I therefore started propagating it by budding and now have about 200 bearing trees, all of which retain the outstanding characteristics of the original tree.

Probably the greatest difference between my new variety and the J. H. Hale lies in the maturity date—my variety ripening 3 or 4 weeks earlier than J. H. Hale, thus enabling the peach canning season to be greatly lengthened.

One of the important improvements found in this variety is its hardiness which is very much greater than that of the J. H. Hale, the latter not being sufficiently hardy for many climates where peaches are ordinarily grown. Its growth is also much more rapid than J. H. Hale. Three-year-old trees of the new variety growing on my ranch are fully one-third larger than J. H. Hale trees of the same age grown under similar conditions.

This new peach is not quite so firm as the J. H. Hale but is sufficiently firm to make an excellent canning peach without being hard.

These qualities, together with the fact that it has a sprightly flavor, make this new peach an excellent canning peach which, in my opinion and the opinion of a number of experts, is much superior to the flavor of J. H. Hale fruit.

The original illustration accompanying this application shows a side view and cross section view of a fully ripened specimen of this variety of peach, slightly enlarged, and in approximately its natural colors.

The tree of this variety differs very little in general appearance from the J. H. Hale, and any standard description of the J. H. Hale tree would apply to the new variety, insofar as appearance is concerned. But there are two very important differences in the invisible qualities. The new variety grows much more rapidly and is much more hardy than the J. H. Hale. And of course the difference in maturity date is also a differing invisible quality.

Blossoms of my new variety are small and of a dull color—almost indentical in appearance to the blossoms of J. H. Hale. They are apparently self-fertile inasmuch as about 200 trees have borne an excellent crop although there were no other peach trees in close proximity to them.

The fruit of the new variety is described in detail as follows:

Maturity: Three to four weeks earlier than J. H. Hale.

Size: Very large; 3¼ inches radial diameter and only slightly less in axial diameter.

Shape: Roundish but with apex end divided into approximately equal halves by deep suture which diminishes at stem end.

Cavity: Deep; wide.

Skin: Pubescence medium, but greater than that of J. H. Hale; thick; tough.

Flesh: Juicy; fine-grained; moderately firm; Light Orange Yellow to Deep Chrome (Plate III), with slight amount of red next the pit.

Flavor: Sprightly; very pleasing.

Stone: Free; halves symmetrical but each half of uneven shape; deeply grooved and pitted; flattened at base.

*Comparison with J. H. Hale*

Although my new variety is more like J. H. Hale than any other known peach variety, there are a number of differences, the most important being as follows:

1. My variety grows more rapidly.
2. My variety is considerably more hardy.
3. The fruit of my variety ripens three to four weeks earlier than that of J. H. Hale.
4. The fruit of my variety has a heavier fuzz.
5. The fruit of my variety is more tart or sprightly.
6. The fruit of my variety is slightly less firm and hard.

Having thus disclosed my discovery, I claim:

The new and distinct variety of peach tree of the J. H. Hale type herein disclosed, characterized particularly by its hardy and rapid growth; the early ripening season of its fruit; and its fruit with excellent, sprightly flavor, moderately firm texture; with deep yellow flesh into which the red next the pit penetrates but slightly and in which red is almost completely absent when fruit is canned.

HERBERT W. DONAHEY.